(12) United States Patent
Mochon

(10) Patent No.: US 9,414,558 B2
(45) Date of Patent: Aug. 16, 2016

(54) OAT PLANTS HAVING INCREASED BETA-GLUCAN LEVELS

(71) Applicant: Wisconsin Alumni Research Foundation, Madison, WI (US)

(72) Inventor: John Mochon, Verona, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 178 days.

(21) Appl. No.: 14/185,837

(22) Filed: Feb. 20, 2014

(65) Prior Publication Data

US 2014/0304851 A1    Oct. 9, 2014

Related U.S. Application Data

(60) Provisional application No. 61/809,146, filed on Apr. 5, 2013.

(51) Int. Cl.
*A01H 5/10* (2006.01)

(52) U.S. Cl.
CPC ...................................... *A01H 5/10* (2013.01)

(58) Field of Classification Search
None
See application file for complete search history.

(56) References Cited

PUBLICATIONS

Kianian et al, 2000, Theor. Appl. Genet., 101:1039-1048.*
Somers et al, 1994, Improvement of Cereal Quality by Genetic Engineering, 37-46.*
Colleonie-Sirghie et al, 2003, Carbohydrate Polymers, 52:439-447.*
Transcript of Interview with Bill Mochon, "New, heart healthy oat variety nearing release," retrieved from http://news.cals.wisc.edu/2012/04/06/new-heart-healthy-oat-variety-nearing-release-audio/, Apr. 6, 2012.
PVP Application No. 201200097, Oat Variety BetaGene/X8787-1, filed Jan. 30, 2012.

\* cited by examiner

*Primary Examiner* — Jason Deveau Rosen
(74) *Attorney, Agent, or Firm* — Dentons US LLP

(57) ABSTRACT

The invention provides oat seed and plants that have increased beta-glucan levels. The invention further provides seed and plants of the oat variety X8787-1 and progeny produced with at least one of these plants as a parent. The invention also relates to the plants, seeds, and tissue cultures of hybrid oat variety X8787-1.

19 Claims, 2 Drawing Sheets

OAT PLANTS HAVING INCREASED BETA-GLUCAN LEVELS

CROSS REFERENCE TO RELATED APPLICATIONS

This application claims the benefit of U.S. Provisional Application No. 61/809,146, filed Apr. 5, 2013, herein incorporated by reference in its entirety.

BACKGROUND OF THE INVENTION

1. Field of the Invention

The present invention relates to the field of plant breeding and, more specifically, to the development of oat plants that produce high levels of beta-glucan.

2. Background of the Invention

The goal of field crop breeding is to combine various desirable traits in a single variety/hybrid. Such desirable traits may include greater yield, resistance to insects or pests, tolerance to heat and drought, better agronomic quality, higher nutritional value, growth rate, and fruit properties.

Breeding techniques take advantage of a plant's method of pollination. There are two general methods of pollination: a plant self-pollinates if pollen from one flower is transferred to the same or another flower of the same plant or plant variety. A plant cross-pollinates if pollen comes to it from a flower on a different plant.

One crop species that has been subject to such breeding programs and is of particular value is oat (*Avena sativa*). Oat is a cereal grain that is grown for its seed and is an important crop for human consumption, as well as a major source of animal feed.

Oats have become an increasingly popular crop worldwide, especially among health-conscious consumers. Oats have been shown to be a "heart healthy" grain, due in part to the health effects of the water soluble fiber, beta-glucan, which is found naturally in oat bran. Beta-glucan is a polysaccharide that has been studied extensively for the last 30 years, and has been shown to be useful in reducing blood cholesterol levels. Because of its cholesterol reducing activity, beta-glucan is the only dietary fiber recognized by the European Food Safety Authority as being able to reduce disease risk.

While breeding efforts to date have provided a number of useful oat lines with beneficial traits, there remains a great need in the art for new lines with further improved traits. Such plants would benefit farmers and consumers alike by improving crop yields and/or quality, as well as providing increased dietary value for both humans and animals.

SUMMARY OF THE INVENTION

In one aspect, the invention provides an oat plant having increased levels of beta-glucan. In another aspect, the invention provides a plurality of such oat plants grown in a field. In one embodiment, a plant of the invention is a plant of the oat variety X8787-1, as well as the derivatives of such plants. Further provided by the invention are plant parts, including cells, plant protoplasts, plant cells of a tissue culture from which oat plants can be regenerated, plant calli, plant clumps, and plant cells that are intact in plants or parts of plants, such as pollen, flowers, seeds, leaves, stems, and the like.

In specific embodiments of the invention, an elevated beta-glucan level provided by the invention comprises, by percent total fiber weight, at least about 5%, 5.5%, 6%, 6.5%, 6.8%, 6.9%, 7%, 7.1%, 7.2%, 7.3%, 7.4%, 7.5%, 7.7%, and 8% or more average beta-glucan content. In further embodiments, an elevated beta-glucan content of about 5% to about 7.1%, about 6% to about 7.5%, about 6.5% to about 7%, about 6% to about 7.1%, and about 6.75% to about 7.1%.

In a further aspect, the invention provides a composition comprising a seed that produces a plant of the invention comprised in plant seed growth media. In certain embodiments, the plant seed growth media is a soil or synthetic cultivation medium. In specific embodiments, the growth medium may be comprised in a container or may, for example, be soil in a field. Plant seed growth media are well known to those of skill in the art and include, but are in no way limited to, soil or synthetic cultivation media. Advantageously, plant seed growth media can provide adequate physical support for seeds and can retain moisture and/or nutritional components. Examples of characteristics for soils that may be desirable in certain embodiments can be found, for instance, in U.S. Pat. Nos. 3,932,166 and 4,707,176. Synthetic plant cultivation media are also well known in the art and may, in certain embodiments, comprise polymers or hydrogels. Examples of such compositions are described, for example, in U.S. Pat. No. 4,241,537.

Another aspect of the invention relates to a tissue culture of regenerable cells of a plant of the invention, as well as plants regenerated therefrom, wherein the regenerated oat plant is capable of expressing all the physiological and morphological characteristics of the plant of the invention.

Yet another aspect of the current invention is an oat plant comprising a single locus conversion, wherein the oat plant is otherwise capable of expressing essentially all the physiological and morphological characteristics of the plant of the invention. In particular embodiments of the invention, the single locus conversion may comprise a transgenic gene which has been introduced by genetic transformation. In still other embodiments of the invention, the single locus conversion may comprise a dominant or recessive allele. The locus conversion may confer potentially any trait upon the single locus converted plant, including nutritional value, herbicide resistance, insect resistance, resistance to bacterial, fungal, or viral disease, male fertility or sterility, and improved nutritional quality.

Still yet another aspect of the invention relates to a first generation ($F_1$) hybrid oat seed produced by crossing a plant of the invention to a second oat plant. Also included in the invention are the $F_1$ hybrid oat plants grown from the hybrid seed produced by such crossing. Still further included in the invention are the seeds of an $F_1$ hybrid plant.

Still yet another aspect of the invention is a method of producing oat seeds comprising crossing a plant of the invention to any second oat plant, including itself or another plant of the invention. In particular embodiments of the invention, the method of crossing comprises the steps of (a) planting seeds of a plant of the invention; (b) cultivating oat plants resulting from said seeds until said plants bear flowers; (c) allowing fertilization of the flowers of said plants; and d) harvesting seeds produced from said plants.

Still yet another aspect of the invention is a method of producing hybrid oat seeds comprising crossing a plant of the invention to a second, distinct oat plant which is nonisogenic to the plant of the invention. In particular embodiments, the crossing comprises the steps of (a) planting seeds of a plant of the invention and a second, distinct oat plant, (b) cultivating the oat plants grown from the seeds until the plants bear flowers; (c) cross-pollinating a flower on one of the two plants with the pollen of the other plant, and (d) harvesting the seeds resulting from the cross pollinating.

Still yet another aspect of the invention is a method for developing an oat plant in an oat breeding program comprising: obtaining an oat plant, or its parts, according to the invention; and employing said plant or parts as a source of breeding material using plant breeding techniques. In the method, the plant breeding techniques may be selected, for example, from the group consisting of recurrent selection, mass selection, bulk selection, backcrossing, pedigree breeding, genetic marker-assisted selection, and genetic transformation. In certain embodiments of the invention, the oat plant of the invention is used as a male or female parent.

Still yet another aspect of the invention is a method of producing an oat plant derived from a plant provided herein, the method comprising the steps of: (a) preparing a progeny plant derived from a plant of the invention by crossing the plant with a second oat plant; and (b) crossing the progeny plant with itself or a second plant to produce a progeny plant of a subsequent generation which is derived from a plant of the invention. In one embodiment of the invention, the method further comprises: (c) crossing the progeny plant of a subsequent generation with itself or a second plant; and (d) repeating steps (b) and (c) for, in some embodiments, at least 2, 3, 4 or more additional generations to produce an inbred oat plant derived from a plant of the invention. Also provided by the invention is a plant produced by this and the other methods of the invention.

In another embodiment of the invention, the method of producing an oat plant derived from a plant of the invention further comprises: (a) crossing a derived oat plant with itself or another oat plant to yield additional derived progeny oat seed; (b) growing the progeny oat seed of step (a) under plant growth conditions to yield additional derived oat plants; and (c) repeating the crossing and growing steps of (a) and (b) to generate further oat plants. In specific embodiments, steps (a) and (b) may be repeated at least 1, 2, 3, 4, or 5 or more times as desired. The invention still further provides an oat plant produced by this and the foregoing methods.

Other objects, features and advantages of the present invention will become apparent from the following detailed description. It should be understood, however, that the detailed description and any specific examples provided, while indicating specific embodiments of the invention, are given by way of illustration only, since various changes and modifications within the spirit and scope of the invention will become apparent to those skilled in the art from this detailed description.

DETAILED DESCRIPTION OF THE INVENTION

The invention provides oat plants (*Avena sativa*) having increased beta-glucan levels. Plants of the present oat variety have been shown to produce elevated levels of beta-glucan. Production of plants with increased levels of beta-glucan demonstrate an important advance over currently available oat varieties, as this would allow companies manufacturing oats and/or oat-containing products to maintain labeling these products as "heart healthy" while reducing the overall amount of oats needed to produce the same level of beta-glucan in their food as the current industry standard.

Origin and Breeding History

An exemplary oat variety produced according to the invention is X8787-1. The pedigree of oat variety X8787-1 is: X7535-9/X7395-4.

Workers in the Department of Agronomy, at the University of Wisconsin-Madison, developed Variety X8787-1. The breeding history of variety X8787-1 is unique in that: (1) both of the parental lines had progenitors that were a 6× amphiploid from a tetraploid×diploid interploidy cross; and (2) irradiation with thermal neutrons in 1968 was a key step in stabilizing genes for crown (leaf) rust resistance from the *Avena strigosa* progenitors.

Figure 1:
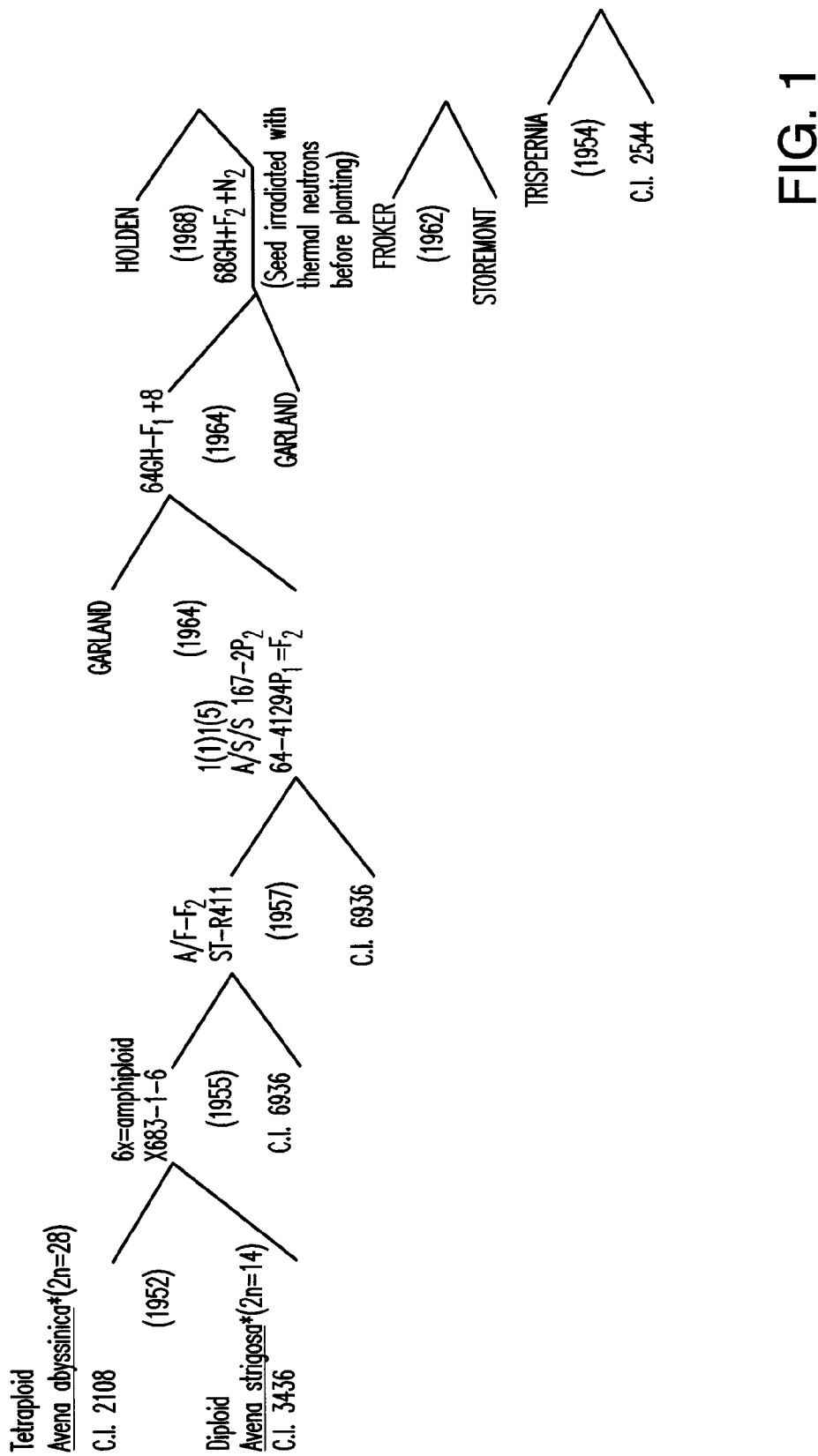
FIG. 1—Shows the pedigree and chronology of crosses for Oat Variety X8787-1.
Figure 1:
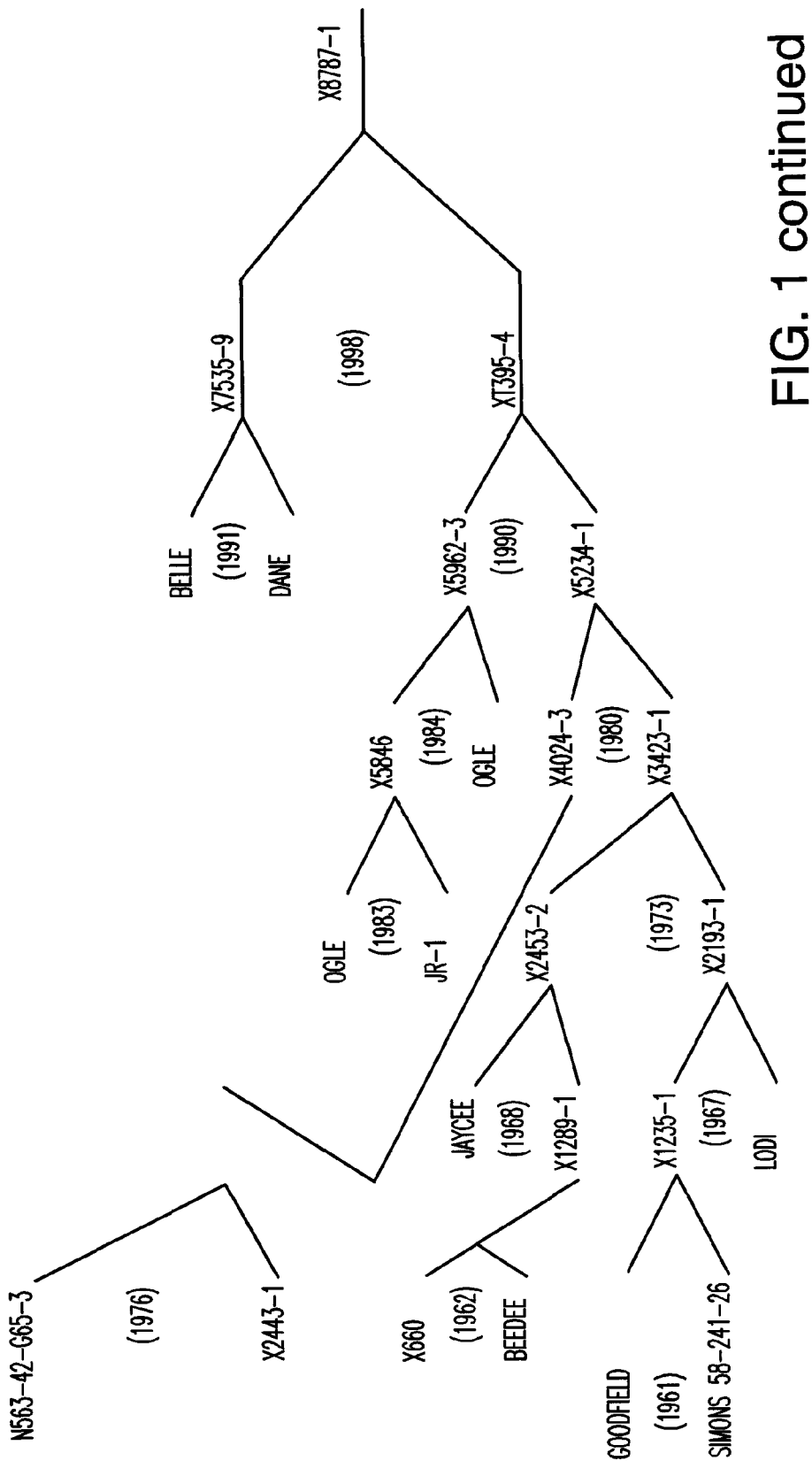

The final cross, X7535-9/X7395-4, was made in the 1998 spring greenhouse. X7535-9 was a Wisconsin experimental oat line (Belle/Dane) that was never entered in the Uniform Oat Performance Nursery (a sibling, X7535-14 was entered in the 2001 UMOPN). Belle, the X7535-9 female parent, contained the 6× amphiploid and the irradiated genetics described above. X7395-4 was a Wisconsin experimental oat line that was never entered in the Uniform Oat Performance Nursery. The pedigree shown in FIG. 1 displays the progenitors that contained the 6× amphiploid and irradiated material for X7395-4.

The pedigree method of plant breeding was strictly followed, and the chronology of progeny generations resulting from the final cross, X7535-9/X7395-4, is listed below:

| | |
|---|---|
| Final cross | 1998 spring greenhouse |
| $F_1$ plants | 1998 field nursery row 12043 |
| $F_2$ population (10-ft. row) | 1999 field nursery row 15170 |
| $F_3$ line (5-ft. row) | 2000 field nursery row 6307 |
| $F_4$ line (5-ft. row) | 2001 field nursery row 5379 |
| $F_5$ line (5-ft. row) | 2002 field nursery row 4118 |
| $F_6$ line (5-ft. row) | 2003 field nursery row 3179 |

Individual panicles were selected from generations $F_2$ through $F_5$, and then all plants in the 2003 $F_6$ line (row) 3179 were cut and threshed in bulk. This population was tested as selection X8787-1, which has subsequently become known as X8787-1.

| | | |
|---|---|---|
| X8787-1 ($F_7$) | 2004: | Preliminary yield trial at Madison (triplicate early-maturity series) |
| X8787-1 ($F_8$) | 2005: | Advanced to main Madison performance trial. |
| | 2006: | Continued in the Madison yield trial and advanced to the Wisconsin ARS statewide trials, advanced to the Arlington drill plots (5 ft. × 40 ft. plots, four replications). |
| X8787-1 | 2007: | Continued in all of the above trials. |
| X8787-1 | 2008: | Continued in all of the above trials, and entered in the USDA Uniform Midseason Oat Performance Nursery (a large multi-state trial), also a $\frac{1}{16}$ acre seed increase. |
| X8787-1 | 2009: | Continued in all of the above trials, plus a 3-acre seed increase (Breeders Seed). |
| X8787-1 | 2010: | Continued in Madison, ARS statewide, Arlington drill plots and the UMOPN performance trials. |
| X8787-1 | 2011: | Continued in all of the above trials except the UMOPN, plus a 30 acre seed increase (Foundation Seed). |
| X8787-1 | 2012: | Certified seed production. |

The primary selection criteria, in the $F_2$ population and in later generations, were resistance to crown (leaf) rust, productive agronomic traits such as yield, and high grain (kernel) quality as measured by test weight, groat percentage, and kernel and groat characteristics.

Traits that were closely monitored in all performance trials were grain yield, test weight, straw strength, maturity, response to diseases, especially crown rust and barley yellow dwarf virus (BYDV), and grain quality factors such as groat percentage and groat protein percentage. High yields, good test weights, high % beta glucan, strong straw, good resistance to crown rust, and good tolerance to BYDV all characterized the performance X8787-1.

The field of Breeders Seed (2009) and the Foundation Seed production field (2011) were inspected repeatedly by the foundation seed program field inspectors. X8787-1 has demonstrated stability for all phenotypic and genotypic plant characteristics consistent with normal environmental influences.

The kernels of X8787-1 are well filled, yellow in color, and non-fluorescent. A stable population of fluorescent seed, at a frequency of 0.09%, has been noted.

X8787-1 has been uniform and stable, and has had no "variants" or "off-types," noted since the line was advanced to the main performance trial at Madison in 2005. At that time, it was an $F_8$ and has since been grown an additional six generations through 2011.

Physiological and Morphological Characteristics

In accordance with one aspect of the present invention, there is provided a plant having the physiological and morphological characteristics of oat variety X8787-1. A description of the physiological and morphological characteristics of oat variety X8787-1 is presented in Table 1.

TABLE 1

Physiological and Morphological Characteristics of Oat Variety X8787-1

| Phenotype: | Variety X8787-1 |
|---|---|
| Growth Habit: | Spring |
| Juvenile Growth: | Erect |
| Days to 50% Flowering: | 57 |
| Maturity Season: | Late |
| Plant Height: | 91 cm |
| Stem Diameter: | Medium |
| Stem Hairiness at Upper Culm Nodes: | Hairy |
| Mature Stem Color: | Yellow |
| Leaf Carriage: | Erect |
| Leaf Color: | Dark Green |
| Leaf Width: | 14 mm |
| Leaf Ligule: | Present |
| Leaf Margin: | Glabrous |
| Leaf Sheath: | Hairless |
| Head Panicle Shape: | Equilateral |
| Attachment of Lower Whorl of Branches: | First Node |
| Head Panicle Size: | Medium |
| Head Panicle Width: | Midbroad |
| Head Panicle Length: | 27 cm |
| Position of Branches: | Spreading |
| Number of Branches: | 18 |
| Number of Whorls on Branches: | 5 |
| Rachis: | Erect |
| Second Floret Rachilla Segment: | Hairless |
| Second Floret Rachilla Segment Length: | 2.4 mm |
| Spikelet Separation by: | Fracture |
| Floret Separation by: | Disarticulation |
| Florets per Spikelet: | 2.6 |
| Glume Color: | Striped |
| Glume Width: | 8 mm |
| Glume Length: | 21 mm |
| Number of Veins on Glumes: | 8 |
| Lemma Color: | Yellow |
| Lemma Length: | 16 mm |
| Hairiness of Lemma Dorsal Surface: | Hairless |
| Awn Occurrence: | Infrequent |
| Awn Type: | Non-twisted |
| Awn Length: | 9 mm |
| Seed Fluorescence Under UV Light: | Non-fluorescent |
| Seed Basal Hair: | Absent |
| Seed Weight Per 1000 Seeds: | 43.7 g |
| Seed Groat Protein: | 14.9% |
| Seed Groat Weight: | 38 mg |
| Seed Groat Oil: | 5.9% |

*These are typical values. Values may vary due to environment. Other values that are substantially equivalent are also within the scope of the invention.

Oat Variety X8787-1 has been determined to be resistant to Halo Blight and races of crown rust (CRS) that are general to Wisconsin, Minnesota, Iowa, South Dakota, North Dakota, and New York. Variety X8787-1 has also been determined to be susceptible to Yellow Dwarf Virus and *Septoria* Leaf Blotch.

Oat variety X8787-1 plants can be stably produced by growing the seed, such as that deposited with the ATCC.

Breeding Oat Varieties

One aspect of the present invention provides methods for crossing a plant of this invention with itself or a second plant and the seeds and plants produced by such methods. These methods can be used for propagation of an oat variety, such as variety X8787-1, or can be used to produce hybrid oat seeds and the plants grown therefrom. For example, hybrid seeds may be produced by crossing a plant of the invention with a second oat parent line.

The development of further varieties using one or more starting varieties is well known in the art. In accordance with the invention, novel varieties may be created by crossing a starting line such as a plant of the invention followed by multiple generations of breeding according to such well-known methods. New varieties may be created by crossing with any second plant. In selecting such a second plant to cross for the purpose of developing novel lines, it may be desired to choose those plants which either themselves exhibit one or more selected desirable characteristics or which exhibit the desired characteristic(s) when in hybrid combination. Once initial crosses have been made, inbreeding and selection take place to produce new varieties. For development of a uniform line, often five or more generations of selfing and selection are involved.

Uniform lines of new varieties may also be developed by way of double-haploids. This technique allows the creation of true breeding lines without the need for multiple generations of selfing and selection. In this manner, true breeding lines can be produced in as little as one generation. Haploid embryos may be produced from microspores, pollen, anther cultures, or ovary cultures. The haploid embryos may then be doubled autonomously, or by chemical treatments (e.g. colchicine treatment). Alternatively, haploid embryos may be grown into haploid plants and treated to induce chromosome doubling. In either case, fertile homozygous plants are obtained. In accordance with the invention, any of such techniques may be used in connection with a plant provided herein and progeny thereof to achieve a homozygous line.

New varieties may be created, for example, by crossing a plant of the invention with any second plant and selection of progeny in various generations and/or by doubled haploid technology. In choosing a second plant to cross for the purpose of developing novel lines, it may be desired to choose those plants which either themselves exhibit one or more selected desirable characteristics or which exhibit the desired characteristic(s) in progeny. After one or more lines are crossed, true-breeding lines may be developed.

Backcrossing can also be used to improve an inbred plant. Backcrossing transfers a specific desirable trait from one inbred or non-inbred source to an inbred that lacks that trait. This can be accomplished, for example, by first crossing a superior inbred (A) (recurrent parent) to a donor inbred (non-recurrent parent), which carries the appropriate locus or loci for the trait in question. The progeny of this cross are then mated back to the superior recurrent parent (A) followed by selection in the resultant progeny for the desired trait to be transferred from the non-recurrent parent. After five or more backcross generations with selection for the desired trait, the progeny are heterozygous for loci controlling the characteristic being transferred, but are like the superior parent for most or almost all other loci. The last backcross generation would be selfed to give pure breeding progeny for the trait being transferred.

The variety of the present invention is particularly well suited for the development of new varieties based on the elite nature of the genetic background of the variety. In selecting a second plant to cross with a plant of the invention for the purpose of developing novel oat lines, it will typically be preferred to choose those plants which either themselves exhibit one or more selected desirable characteristics or which exhibit the desired characteristic(s) when in hybrid combination. Examples of desirable characteristics may include, but are not limited to, nutritional content, seed yield, size, shape and uniformity, early maturity, disease resistance, herbicide tolerance, seedling vigor, adaptability for soil conditions, adaptability for climate conditions, for example heat and/or cold tolerance, and uniform plant height.

Performance Characteristics of Oat Variety X8787-1

As described herein, oat variety X8787-1 exhibits desirable agronomic traits, particularly increased levels of beta-glucan. In Wisconsin statewide tests, variety X8787-1 demonstrated consistently high grain yields, ranking third highest in 2009-2011 statewide yield averages. Test weights were good, similar to those of comparison variety Vista, at 36.3 lbs./bushel in 2009-2011 statewide averages. Heading date in variety X8787-1 is approximately 1 day earlier than Vista and 2 days earlier than comparison variety Drumlin. Variety X8787-1 is closest in height to Drumlin and approximately 4 inches shorter when compared to Vista. Lodging is approximately equal to that of comparison variety Saber, less than Drumlin and Vista, and slightly greater than comparison variety Esker, ranking fourth best in the 2009-2011 statewide averages. BYDV tolerance is comparable to that of Esker and Drumlin. In addition, crown rust resistance was very good, with variety X8787-1 showing resistance to 78% of races tested.

In the UNIFORM regional trials of 2008-2010, variety X8787-1 was ranked number 5 for three-year yield, number 11 for three-year heading date, and number 7 for three-year height. Variety X8787-1 was ranked number 1 for beta-glucan percentage for three years in a row, with beta-glucan as high as 7.3%. In Minnesota statewide trials in 2009-2011, Variety X8787-1 tied for second place for yield in 2009, took third place for yield in 2010 and second place for 2-year yield, and in 2011, variety X8787-1 was second in both yield and 3-year yield.

Oat variety X8787-1 is most similar to the previously existing variety Vista. Both X8787-1 and Vista are considered later maturity oats. Characteristics by which X8787-1 differs from Vista are as follows:

In field trials in the upper Midwest, X8787-1 has shown good resistance to the prevalent races of crown rust (CRS), while Vista has been more susceptible (Table 3). The tests each year are rated on a 1 to 5 scale, with a lower number indicating better tolerance to the disease. Ratings are averages of Madison and Arlington (2 locations) scores over 3 years (six station years).

TABLE 3

Performance Data For Oat Variety X8787-1

|  | 2009 | 2010 | 2011 | 3 yr. AVG. |
|---|---|---|---|---|
| Vista | 1.5 | 1.8 | 2.4 | 1.9 |
| X8787-1 | 1.1 | 1.5 | 1.5 | 1.4 |
| CRS diff. | 0.4 | 0.3 | 0.9 | 0.5 |
| Entries | 24 | 25 | 27 |  |
| Reps | 7 | 8 | 8 |  |
| L.S.D. .05 | 0.35 | 0.29 | 0.47 | 0.08 |
| C.V. % | 26.2 | 16.4 | 23.4 | 22.0 |

X8787-1 has been consistently, significantly shorter than Vista, as indicated in the height readings given in Table 4 below. The data is taken from trials grown at seven locations in Wisconsin during 2009, 2010, and 2011 (21 station years). The full data set is shown in Table 2 below.

TABLE 4

Performance Data For Oat Variety X8787-1
2009-2011 height averages (inches):

| Vista: | 40.0 |
|---|---|
| X8787-1: | 36.2 |
| Height difference: | 3.8 |
| Number of Entries: | 34-36 |
| Number of Repetitions: | 4 |
| 2009-2011 3 yr. height avg. L.S.D.$_{.05}$: | 0.63 |
| 2009-2011 3 yr. height avg. C.V. %: | 5.73 |

TABLE 2

Grain yield, agronomic, and disease characteristics for twelve oat varieties and Wisconsin test selection X8787-1 in multiple statewide tests in 2009, 2010, and 2011.

| Variety | YIELD bu./a | TEST WEIGHT lbs./bu. | HEADING DATE June | HEIGHT inches | LODGING % | BYDV 1-9 | CRS 1-5 |
|---|---|---|---|---|---|---|---|
| Number of tests | 21 | 21 | 18 | 21 | 20 | 6 | 6 |
| X8787-1 | 102.8 | 36.3 | 26 | 36.2 | 36 | 1.8 | 1.4 |
| Badger | 88.9 | 37.9 | 20 | 32.8 | 38 | 2.4 | 1.4 |
| Colt | 85.2 | 39.8 | 21 | 36.3 | 40 | 2.6 | 2.0 |
| Dane | 76.0 | 36.8 | 19 | 34.5 | 44 | 2.4 | 2.5 |
| Esker | 87.8 | 37.1 | 23 | 35.4 | 37 | 1.9 | 2.4 |
| Excel | 91.6 | 36.6 | 24 | 35.0 | 38 | 1.7 | 2.0 |
| Kame | 80.8 | 34.3 | 22 | 33.8 | 45 | 3.1 | 2.5 |
| Ogle | 90.5 | 36.4 | 24 | 35.4 | 42 | 2.3 | 2.5 |
| Saber | 91.5 | 37.5 | 22 | 34.0 | 35 | 1.7 | 2.5 |
| Shelby 427 | 94.2 | 40.3 | 23 | 37.8 | 40 | 1.3 | 1.1 |
| Drumlin | 92.2 | 35.7 | 28 | 36.4 | 46 | 1.5 | 2.0 |
| Rockford | 102.8 | 39.9 | 30 | 40.6 | 32 | 2.3 | 1.1 |
| Vista | 92.0 | 36.8 | 27 | 40.0 | 49 | 2.7 | 1.9 |
| Mean | 89.5 | 37.4 | 23.5 | 36.0 | 40.3 | 2.2 | 1.9 |

TABLE 5

Grain yields (bu/a) for twelve oat varieties and Wisconsin test selection
X8787-1 in trials at seven Wisconsin locations in 2009, 2010, and 2011.

| Variety | ARLINGTON | MADISON | LANCASTER | MARSHFIELD | SPOONER | STURGEON BAY | CHILTON | 7 location mean |
|---|---|---|---|---|---|---|---|---|
| Number of tests | 3 | 3 | 3 | 3 | 3 | 3 | 3 | 21 |
| X8787-1 | 126.4 | 126.5 | 95.0 | 107.0 | 73.2 | 92.2 | 99.2 | 102.8 |
| Badger | 124.1 | 109.0 | 83.4 | 77.6 | 54.8 | 97.7 | 75.7 | 88.9 |
| Colt | 118.3 | 103.1 | 69.2 | 77.9 | 56.7 | 93.9 | 77.0 | 85.2 |
| Dane | 90.1 | 87.3 | 73.5 | 77.9 | 35.0 | 98.4 | 69.5 | 76.0 |
| Esker | 103.9 | 111.0 | 88.7 | 82.9 | 54.7 | 102.9 | 70.5 | 87.8 |
| Excel | 117.2 | 100.8 | 76.8 | 92.6 | 60.8 | 108.6 | 84.3 | 91.6 |
| Kame | 103.1 | 96.9 | 71.8 | 81.4 | 47.6 | 98.7 | 66.5 | 80.8 |
| Ogle | 104.1 | 96.7 | 84.1 | 84.6 | 74.3 | 115.0 | 74.9 | 90.5 |
| Saber | 102.9 | 101.3 | 88.9 | 91.6 | 64.4 | 118.8 | 72.2 | 91.5 |
| Shelby 427 | 130.3 | 121.0 | 79.6 | 85.9 | 65.0 | 101.2 | 76.5 | 94.2 |
| Drumlin | 104.0 | 104.6 | 82.5 | 102.2 | 70.2 | 100.1 | 81.4 | 92.2 |
| Rockford | 130.5 | 128.3 | 96.0 | 97.0 | 74.7 | 94.3 | 99.2 | 102.8 |
| Vista | 106.8 | 107.6 | 86.0 | 96.6 | 74.1 | 93.3 | 79.7 | 92.0 |
| Mean | 111.3 | 105.6 | 81.7 | 87.3 | 61.0 | 101.9 | 77.3 | 89.5 |
| L.S.D | 7.9 | 9.1 | 9.3 | 12.4 | 12.0 | 12.0 | 9.1 | 3.7 |

Further Embodiments of the Invention

The invention also provides seed of a plant of the invention. The oat seed of the invention may or may not be provided as an essentially homogeneous population of oat seed. Essentially homogeneous populations of seed are generally free from substantial numbers of other seed. Therefore, a seed of the invention may, in one embodiment, be defined as forming at least about 97% of the total seed, including at least about 98%, 99%, or more of the seed. In certain embodiments, the population of oat seed may be particularly defined as being essentially free from hybrid seed. The seed population may be separately grown to provide an essentially homogeneous population of oat plants.

As used herein, "oat plant" also includes plants modified to include at least a first desired heritable trait. Such plants may, in one embodiment, be developed by a plant breeding technique called backcrossing, wherein essentially all of the desired morphological and physiological characteristics of a variety are recovered, in addition to a genetic locus transferred into the plant via the backcrossing technique. The term "single locus converted plant" as used herein refers to those oat plants which are developed by a plant breeding technique called backcrossing, wherein essentially all of the desired morphological and physiological characteristics of a variety are recovered in addition to the single locus transferred into the variety via the backcrossing technique.

Introgression of a desired trait into a plant according to the present invention may be accomplished by any methods known in the art. For example, marker-assisted introgression may involves the transfer of a chromosomal region, defined by one or more markers, from one plant or germplasm to a second plant or germplasm. Offspring of a cross that contain the introgressed genomic region can be identified by the combination of markers characteristic of the desired introgressed genomic region from a first germplasm (e.g., a plant or germplasm having a desired trait or phenotype) and both linked and unlinked markers characteristic of the desired genetic background of a second germplasm.

Backcrossing methods can be used with the present invention to improve or introduce a characteristic into the present variety. The parental oat plant that contributes the locus for the desired characteristic is termed the nonrecurrent or donor parent. This terminology refers to the fact that the nonrecurrent parent is used one time in the backcross protocol and therefore does not recur. The parental oat plant to which the locus or loci from the nonrecurrent parent are transferred is known as the recurrent parent, as it is used for several rounds in the backcrossing protocol.

In a typical backcross protocol, the original variety of interest (recurrent parent) is crossed to a second variety (nonrecurrent parent) that carries the single locus of interest to be transferred. The resulting progeny from this cross are then crossed again to the recurrent parent, and the process is repeated until an oat plant is obtained wherein essentially all of the desired morphological and physiological characteristics of the recurrent parent are recovered in the converted plant, in addition to the single transferred locus from the nonrecurrent parent.

The selection of a suitable recurrent parent is an important step for a successful backcrossing procedure. The goal of a backcross protocol is to alter or substitute a single trait or characteristic in the original variety. To accomplish this, a single locus of the recurrent variety is modified or substituted with the desired locus from the nonrecurrent parent, while retaining essentially all of the rest of the desired genetic material and therefore the desired physiological and morphological constitution of the original variety. The choice of the particular nonrecurrent parent will depend on the purpose of the backcross; one of the major purposes is to add some commercially desirable trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

In one embodiment, progeny oat plants of a backcross in which oat variety X8787-1 is the recurrent parent comprise (i) the desired trait from the non-recurrent parent and (ii) all of the physiological and morphological characteristics of a plant of the invention as determined at the 5% significance level when grown in the same environmental conditions.

Oat varieties can also be developed from more than two parents. The technique, known as modified backcrossing, uses different recurrent parents during the backcrossing. Modified backcrossing may be used to replace the original recurrent parent with a variety having certain more desirable characteristics, or multiple parents may be used to obtain different desirable characteristics from each.

Many single locus traits have been identified that are not regularly selected for in the development of a new inbred but that can be improved by backcrossing techniques. Single locus traits may or may not be transgenic; examples of these traits include, but are not limited to, male sterility, herbicide tolerance, resistance to bacterial, fungal, or viral disease, insect resistance, restoration of male fertility, modified fatty acid or carbohydrate metabolism, and enhanced nutritional quality. These traits comprise genes generally inherited through the nucleus.

Direct selection may be applied where the single locus acts as a dominant trait. An example of a dominant trait is the anthracnose resistance trait. For this selection process, the progeny of the initial cross are sprayed with anthracnose spores prior to the backcrossing. The spraying eliminates any plants which do not have the desired anthracnose resistance characteristic, and only those plants which have the anthracnose resistance gene are used in the subsequent backcross. This process is then repeated for all additional backcross generations.

Selection of oat plants for breeding is not necessarily dependent on the phenotype of a plant and instead can be based on genetic investigations. For example, one can utilize a suitable genetic marker which is closely genetically linked to a trait of interest. One of these markers can be used to identify the presence or absence of a trait in the offspring of a particular cross, and can be used in selection of progeny for continued breeding. This technique is commonly referred to as marker-assisted selection. Any other type of genetic marker or other assay which is able to identify the relative presence or absence of a trait of interest in a plant can also be useful for breeding purposes. Procedures for marker-assisted selection applicable to the breeding of oats are well known in the art. Such methods will be of particular utility in the case of recessive traits and variable phenotypes, or where conventional assays may be more expensive, time consuming or otherwise disadvantageous. Types of genetic markers which could be used in accordance with the invention include, but are not necessarily limited to, Simple Sequence Length Polymorphisms (SSLPs) (Williams et al., 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., 1998).

Plants Derived by Genetic Engineering

Many useful traits that can be introduced by backcrossing, as well as directly into a plant, are those which are introduced by genetic transformation techniques. Genetic transformation may therefore be used to insert a selected transgene into the oat variety of the present invention, and/or a parent of a hybrid oat variety produced according to the invention, or may, alternatively, be used for the preparation of transgenes that can be introduced by backcrossing. Methods for the transformation of plants, including oats, are well known to those of skill in the art.

Most research efforts have been directed at developing *Agrobacterium*-mediated transformation methods with relatively little emphasis on direct gene transfer techniques. Procedures for the transformation of *A. sativa* would be known to one of skill in the art. Principal difficulties in such techniques may relate to combining efficient plant regeneration with gene transfer. Inefficient selection can result in the regeneration of chimeric plants upon *Agrobacterium tumefaciens*-mediated transformation. Promising results have been obtained with *Agrobacterium rhizogenes*-mediated transformation. Few agronomically useful characters have been introduced, the majority of research having been confined to the introduction of marker and reporter genes.

Generally speaking, techniques which may be employed for the genetic transformation of oat include, but are not limited to, electroporation, microprojectile bombardment, *Agrobacterium*-mediated transformation and direct DNA uptake by protoplasts.

To effect transformation by electroporation, one may employ either friable tissues, such as a suspension culture of cells or embryogenic callus, or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

A particularly efficient method for delivering transforming DNA segments to plant cells is microprojectile bombardment. In this method, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a surface covered with target oat cells. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large.

Microprojectile bombardment techniques are widely applicable, and may be used to transform virtually any plant species.

*Agrobacterium*-mediated transfer is another widely applicable system for introducing gene loci into plant cells. An advantage of the technique is that DNA can be introduced into whole plant tissues, thereby bypassing the need for regeneration of an intact plant from a protoplast. Modern *Agrobacterium* transformation vectors are capable of replication in *E. coli* as well as *Agrobacterium*, allowing for convenient manipulations (Klee et al., 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described have convenient multi-linker regions flanked by a promoter and a polyadenylation site for direct expression of inserted polypeptide coding genes. Additionally, *Agrobacterium* containing both armed and disarmed Ti genes can be used for transformation.

In those plant strains where *Agrobacterium*-mediated transformation is efficient, it is the method of choice because of the facile and defined nature of the gene locus transfer. The use of *Agrobacterium*-mediated plant integrating vectors to introduce DNA into plant cells is well known in the art (Fraley et al., 1985; U.S. Pat. No. 5,563,055).

Transformation of plant protoplasts also can be achieved using methods based on calcium phosphate precipitation, polyethylene glycol treatment, electroporation, and combinations of these treatments (see, e.g., Potrykus et al., 1985; Omirulleh et al., 1993; Fromm et al., 1986; Uchimiya et al., 1986; Marcotte et al., 1988). Transformation of plants and expression of foreign genetic elements is exemplified in Choi et al. (1994), and Ellul et al. (2003).

A number of promoters have utility for plant gene expression for any gene of interest including, but not limited to, selectable markers, scoreable markers, genes for pest tolerance, disease resistance, nutritional enhancements, and any other gene of agronomic interest. Examples of constitutive promoters useful for oat plant gene expression include, but are not limited to, the cauliflower mosaic virus (CaMV) P-35S promoter, which confers constitutive, high-level expression in most plant tissues (see, e.g., Odel et al., 1985), including monocots (see, e.g., Dekeyser et al., 1990; Terada and Shimamoto, 1990); a tandemly duplicated version of the CaMV 35S promoter, the enhanced 35S promoter (P-e35S) the nopaline synthase promoter (An et al., 1988), the octopine synthase promoter; and the figwort mosaic virus (P-FMV) promoter as described in U.S. Pat. No. 5,378,619 and an enhanced version of the FMV promoter (P-eFMV) where the promoter sequence of P-FMV is duplicated in tandem, the cauliflower mosaic virus 19S promoter, a sugarcane bacilliform virus promoter, a commelina yellow mottle virus promoter, and other plant DNA virus promoters known to express in plant cells.

A variety of plant gene promoters that are regulated in response to environmental, hormonal, chemical, and/or developmental signals can be used for expression of an operably linked gene in plant cells, including promoters regulated by (1) heat (Callis et al., 1988), (2) light (e.g., pea rbcS-3A promoter, Kuhlemeier et al., 1989; maize rbcS promoter, Schaffner and Sheen, 1991; or chlorophyll a/b-binding protein promoter, Simpson et al., 1985), (3) hormones, such as abscisic acid (Marcotte et al., 1989), (4) wounding (e.g., wunl, Siebertz et al., 1989); or (5) chemicals such as methyl jasmonate, salicylic acid, or Safener. It may also be advantageous to employ organ-specific promoters (e.g., Roshal et al., 1987; Schernthaner et al., 1988; Bustos et al., 1989).

Exemplary nucleic acids which may be introduced to the oat variety of this invention include, for example, DNA sequences or genes from another species, or even genes or sequences which originate with or are present in the same species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into an oat plant according to the invention. Non-limiting examples of particular genes and corresponding phenotypes one may choose to introduce into an oat plant include one or more genes for insect tolerance, such as a *Bacillus thuringiensis* (Bt) gene, pest tolerance such as genes for fungal disease control, herbicide tolerance such as genes conferring glyphosate tolerance, and genes for quality improvements such as yield, nutritional enhancements, environmental or stress tolerances, or any desirable changes in plant physiology, growth, development, morphology or plant product(s). For example, structural genes would include any gene that confers insect tolerance including, but not limited to, a *Bacillus* insect control protein gene as described in WO 99/31248, herein incorporated by reference in its entirety, U.S. Pat. No. 5,689,052, herein incorporated by reference in its entirety, U.S. Pat. Nos. 5,500,365 and 5,880,275, herein incorporated by reference it their entirety. In another embodiment, the structural gene can confer tolerance to the herbicide glyphosate as conferred by genes including, but not limited to *Agrobacterium* strain CP4 glyphosate tolerant EPSPS gene (aroA:CP4) as described in U.S. Pat. No. 5,633,435, herein incorporated by reference in its entirety, or glyphosate oxidoreductase gene (GOX) as described in U.S. Pat. No. 5,463,175, herein incorporated by reference in its entirety.

Alternatively, the DNA coding sequences can affect these phenotypes by encoding a non-translatable RNA molecule that causes the targeted inhibition of expression of an endogenous gene, for example via antisense- or cosuppression-mediated mechanisms (see, for example, Bird et al., 1991). The RNA could also be a catalytic RNA molecule (i.e., a ribozyme) engineered to cleave a desired endogenous mRNA product (see, for example, Gibson and Shillito, 1997). Thus, any gene which produces a protein or mRNA which expresses a phenotype or morphology change of interest is useful for the practice of the present invention.

DEFINITIONS

In the description and tables herein, a number of terms are used. In order to provide a clear and consistent understanding of the specification and claims, the following definitions are provided:

Allele: Any of one or more alternative forms of a gene locus, all of which alleles relate to one trait or characteristic. In a diploid cell or organism, the two alleles of a given gene occupy corresponding loci on a pair of homologous chromosomes.

Backcrossing: A process in which a breeder repeatedly crosses hybrid progeny, for example a first generation hybrid ($F_1$), back to one of the parents of the hybrid progeny. Backcrossing can be used to introduce one or more single locus conversions from one genetic background into another.

Crossing: The mating of two parent plants.

Cross-pollination: Fertilization by the union of two gametes from different plants.

Diploid: A cell or organism having two sets of chromosomes.

Emasculate: The removal of plant male sex organs or the inactivation of the organs with a cytoplasmic or nuclear genetic factor conferring male sterility or a chemical agent.

Enzymes: Molecules which can act as catalysts in biological reactions.

$F_1$ Hybrid: The first generation progeny of the cross of two nonisogenic plants.

Genotype: The genetic constitution of a cell or organism.

Haploid: A cell or organism having one set of the two sets of chromosomes in a diploid.

Linkage: A phenomenon wherein alleles on the same chromosome tend to segregate together more often than expected by chance if their transmission was independent.

Marker: A readily detectable phenotype, preferably inherited in codominant fashion (both alleles at a locus in a diploid heterozygote are readily detectable), with no environmental variance component, i.e., heritability of 1.

Phenotype: The detectable characteristics of a cell or organism, which characteristics are the manifestation of gene expression.

Quantitative Trait Loci (QTL): Quantitative trait loci (QTL) refer to genetic loci that control to some degree numerically representable traits that are usually continuously distributed.

Regeneration: The development of a plant from tissue culture.

Resistance: As used herein, the terms "resistance" and "tolerance" are used interchangeably to describe plants that show no symptoms to a specified biotic pest, pathogen, abiotic influence, or environmental condition. These terms are also used to describe plants showing some symptoms but that are still able to produce marketable product with an acceptable yield. Some plants that are referred to as resistant or tolerant are only so in the sense that they may still produce a crop, even though the plants are stunted and the yield is reduced.

Self-pollination: The transfer of pollen from the anther to the stigma of the same plant.

Single Locus Converted (Conversion) Plant: Plants that are developed by a plant breeding technique called backcrossing, wherein essentially all of the desired morphological and physiological characteristics of an oat variety are recovered in addition to the characteristics of the single locus transferred into the variety via the backcrossing technique and/or by genetic transformation.

Substantially Equivalent: A characteristic that, when compared, does not show a statistically significant difference (e.g., p=0.05) from the mean.

Tetraploid: A cell or organism having four sets of chromosomes.

Tissue Culture: A composition comprising isolated cells of the same or a different type or a collection of such cells organized into parts of a plant.

Transgene: A genetic locus comprising a sequence which has been introduced into the genome of an oat plant by transformation.

Triploid: A cell or organism having three sets of chromosomes.

Any embodiment discussed herein with respect to one aspect of the invention applies to other aspects of the invention as well, unless specifically noted.

The term "about" is used to indicate that a value includes the standard deviation of error for the device or method being employed to determine the value. The use of the term "or" in the claims is used to mean "and/or" unless explicitly indicated to refer to alternatives only or the alternatives are mutually exclusive, although the disclosure supports a definition that refers to only alternatives and to "and/or." When used in conjunction with the word "comprising" or other open language in the claims, the words "a" and "an" denote "one or more," unless specifically noted. The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits.

All references cited herein are hereby expressly incorporated herein by reference.

DEPOSIT INFORMATION

Deposit of oat variety X8787-1, which is disclosed above and recited in the claims, will be made with the American Type Culture Collection (ATCC), 10801 University Blvd., Manassas, Va. 20110-2209. The date of deposit is Apr. 28, 2016 and the accession number for the deposited seeds is ATCC Accession No. PTA-123083. Upon issuance of a patent, all restrictions upon the deposits will be removed, and the deposits are intended to meet all of the requirements of 37 C.F.R. §1.801-1.809. The deposits will be maintained in the depository for a period of 30 years, or 5 years after the last request, or for the effective life of the patent, whichever is longer, and will be replaced if necessary during that period.

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. An oat plant of variety X8787-1 having elevated levels of beta-glucan, wherein a sample of seed of said variety has been deposited under ATCC Accession No. PTA-123083.

2. A plurality of plants according to claim 1 grown in a field.

3. A plant part of the plant of claim 1, wherein the plant part comprises at least one cell of said plant.

4. The plant part of claim 3, further defined as pollen, a meristem, a cell, a seed, or an ovule.

5. A seed that produces the plant of claim 1.

6. A method of producing oat seed, the method comprising crossing an oat plant of variety X8787-1 with itself or a second oat plant, wherein a sample of seed of said variety has been deposited under ATCC Accession No. PTA-123083.

7. The method of claim 6, further defined as comprising crossing said oat plant of variety X8787-1 with a second, distinct oat plant to produce an F1 hybrid oat seed.

8. An F1 hybrid oat seed produced by the method of claim 7.

9. A method of producing an oat plant comprising a desired beta-glucan content comprising:
    (a) obtaining the plant according to claim 1,
    (b) applying plant breeding techniques to said plant and progeny thereof, and
    (c) selecting at least one further progeny plant resulting from said step (b) that comprises a desired beta-glucan content.

10. The method of claim 9, wherein said step of obtaining comprises growing said plant of oat variety X8787-1, wherein a sample of seed of said variety has been deposited under ATCC Accession No. PTA-123083.

11. A composition comprising plant tissue of an oat plant according to claim 1, wherein the oat tissue comprises an elevated endogenous level of beta-glucan.

12. The plant of claim 1, defined as comprising a transgene.

13. The plant of claim 1, defined as non-transgenic.

14. A plant produced by introducing a single locus conversion into oat variety X8787-1, or a selfed progeny thereof comprising the single locus conversion, wherein the single locus conversion was introduced into oat variety X8787-1 by backcrossing or genetic transformation and wherein a sample of seed of oat variety X8787-1 has been deposited under ATCC Accession No. PTA-123083.

15. A seed that produces the plant of claim 14.

16. The method of claim 7, wherein the method further comprises:
   (a) crossing a plant grown from said F1 hybrid oat seed with itself or a different oat plant to produce a seed of a progeny plant of a subsequent generation;
   (b) growing a progeny plant of a subsequent generation from said seed of a progeny plant of a subsequent generation and crossing the progeny plant of a subsequent generation with itself or a second plant to produce a progeny plant of a further subsequent generation; and
   (c) repeating steps (a) and (b) using said progeny plant of a further subsequent generation from step (b) in place of the plant grown from said F1 hybrid oat seed in step (a), wherein steps (a) and (b) are repeated with sufficient inbreeding to produce an inbred oat plant.

17. A method of producing a commodity plant product comprising collecting a commodity plant product from the plant of claim 1.

18. The method of claim 17, wherein the commodity plant product is protein concentrate, protein isolate, grain, meal, flour, or oil.

19. An oat commodity plant product produced by the method of claim 17, wherein the commodity plant product comprises at least one cell of oat variety X8787-1, wherein a sample of seed of oat variety X8787-1 has been deposited under ATCC Accession No. PTA-123083.

* * * * *